(12) United States Patent
Itsuji et al.

(10) Patent No.: US 8,144,370 B2
(45) Date of Patent: Mar. 27, 2012

(54) IMAGE FORMING APPARATUS, PRINTING METHOD AND PRINTING APPARATUS

(75) Inventors: Takeaki Itsuji, Hiratsuka (JP); Takehiko Kawasaki, Kamakura (JP); Norio Kaneko, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 1209 days.

(21) Appl. No.: 11/850,256

(22) Filed: Sep. 5, 2007

(65) Prior Publication Data

US 2008/0062470 A1 Mar. 13, 2008

(30) Foreign Application Priority Data

Sep. 12, 2006 (JP) .................................. 2006-246196

(51) Int. Cl.
| | |
|---|---|
| *H04N 1/00* | (2006.01) |
| *G01R 27/32* | (2006.01) |
| *G03G 15/00* | (2006.01) |
| *G06F 3/12* | (2006.01) |
| *G06K 15/00* | (2006.01) |

(52) U.S. Cl. ...... 358/401; 358/1.15; 358/1.16; 324/640; 324/643; 399/44

(58) Field of Classification Search ........ 358/1.11–1.18, 358/401; 324/640; 399/23
See application file for complete search history.

(56) References Cited

U.S. PATENT DOCUMENTS

| | | | | |
|---|---|---|---|---|
| 5,845,529 | A * | 12/1998 | Moshe et al. ..................... 73/73 |
| 6,636,704 | B2 * | 10/2003 | Weaver et al. .................. 399/23 |
| 7,152,861 | B2 | 12/2006 | Kawasaki ..................... 271/262 |
| 7,212,929 | B2 * | 5/2007 | Kaneko et ....................... 702/50 |
| 7,239,817 | B2 | 7/2007 | Kaneko et al. ................... 399/45 |
| 7,296,795 | B2 | 11/2007 | Kawasaki ..................... 271/262 |
| 7,304,291 | B2 * | 12/2007 | Kawasaki et al. ............. 250/221 |
| 2006/0022400 | A1 | 2/2006 | Kawasaki et al. ............. 271/227 |
| 2006/0275045 | A1 | 12/2006 | Kawasaki et al. ................ 399/45 |
| 2007/0036567 | A1 | 2/2007 | Kawasaki et al. ................ 399/45 |
| 2007/0200568 | A1 * | 8/2007 | Shioda et al. .................. 324/640 |
| 2007/0243004 | A1 * | 10/2007 | Kuwasaki ..................... 400/708 |
| 2008/0001348 | A1 | 1/2008 | Kawasaki et al. ............. 271/259 |
| 2009/0322847 | A1 * | 12/2009 | Yamamura .................... 347/130 |

FOREIGN PATENT DOCUMENTS

| | | |
|---|---|---|
| JP | 09-133631 A | 5/1997 |
| JP | 09-236547 A | 9/1997 |
| JP | 2002-292832 | 10/2002 |
| JP | 2002-292832 A | 10/2002 |
| JP | 2005-157601 A | 6/2005 |

* cited by examiner

*Primary Examiner* — Mark K Zimmerman
*Assistant Examiner* — Satwant Singh
(74) *Attorney, Agent, or Firm* — Fitzpatrick, Cella, Harper & Scinto

(57) ABSTRACT

To provide new image forming apparatus and a printing method that can obtain information on image forming by using terahertz waves. An image forming apparatus includes a stock unit for stocking a media stack made of a plurality of media with images formed on; an electromagnetic wave generation unit for generating a terahertz wave to radiate on the media stack; an electromagnetic wave detection unit for detecting the terahertz wave propagated in a laminating direction of the media stack; a memory unit for storing reference data; a processing unit for generating data related to an image forming state from the detection signal from the electromagnetic wave detection unit, information on the number of sheets of the medium, and information on the image formed on the medium; and a comparative unit for comparing the data generated by the processing unit and the reference data stored in the memory unit.

7 Claims, 4 Drawing Sheets

IMAGE FORMING APPARATUS, PRINTING METHOD AND PRINTING APPARATUS

BACKGROUND OF THE INVENTION

1. Field of the Invention

The present invention relates to a printing method and printing apparatus for performing printing by adjusting a print state according to a monitored result, while monitoring the print state of such a medium as a sheet of paper by using a high frequency electromagnetic wave ranging from a millimeter wave to a terahertz wave. More specifically, the present invention relates to a technique appropriate for a printing method and printing apparatus for quickly performing printing on a sheet of paper.

2. Description of the Related Art

Non-destructive examination techniques using high frequency electromagnetic waves with an arbitrary frequency band ranging from a millimeter wave to a terahertz wave (30 GHz to 30 THz) (also referred to 'terahertz wave' in this specification) have been developed. It is known that the terahertz waves include absorption lines for various materials including biomolecular. The frequency region is applied to an imaging technique for performing safe fluoroscopy to replace the X-ray. It is also applied to spectral techniques for examining a binding state of molecules by obtaining an absorbing spectrum or a complex dielectric constant inside an object. Techniques for analyzing biomolecular and techniques for evaluating a carrier density or movement are also candidates as an application of the newly developed techniques.

In the image forming apparatus for forming an image on a sheet of paper like a copy machine or a printer, the print state needs to be always kept equal. Generally, the print state is susceptible to a change in the printing environment both inside and outside the printing apparatus including a change in temperature or humidity. In most cases, the printing condition is adjusted and fit to the change in the printing environment in a detecting manner for detecting such a change in the printing environment. Under such printing conditions, an image is formed on a sheet of paper.

As one of the detecting manners, apparatus for measuring the coating thickness or the moisture content of ink using the terahertz wave is disclosed (Japanese Patent Application Laid-Open No. 2002-292832). The disclosed technique always monitors the coating thickness or the moisture content of ink by using a change in transmittance of the terahertz wave. Then, it controls the print state in an attempt to improve the quality of printed matters by using the monitored result.

SUMMARY OF THE INVENTION

The abovementioned printing method is for serially controlling the print state such that a desired printed result can be obtained, while monitoring a change in a propagation state of the terahertz wave. Specifically, the printing method is for measuring the coating thickness or the moisture content of ink applied to a drum or a sheet of paper in the direction of the coating thickness according to a change in a propagation state of the terahertz wave. The coating thickness in the print region, however, is quite thin for the wavelength of the terahertz wave used in the measurement. That makes a region that effects each other with the terahertz wave narrow. Accordingly, it is difficult to obtain a sufficient change in the propagation state of the terahertz wave.

For the purpose of serially controlling a print state, it is basically desired that image data for a printed matter is the same. The print states need to be compared by the image data of the same printed matter. This is because: If printed matters have different kinds of image data, proportion of a printed region, on which toner or ink are to be applied, and a non-printed region differs among the printed matters. Therefore, the measurements of the print states differ. In other words, the amount of toner or ink that has an effect with the terahertz wave differs according to the proportion of a printed region and a non-printed region. Therefore, the propagation states of the terahertz wave are measured differently even in the print state of the same quality. If the print state is adjusted or controlled based on such a measurement, basically desirable printing conditions are altered. That will degrade the quality of the printed matters as a result.

The printing speed of a printer is about 20 to 30 sheets per minute for an ink jet printer for home use. The speed for a high-speed printer for POD (print on demand) is about 100 to 150 sheets per minute. The printing speeds have been becoming faster. If such printers control a print state for each printed matter by using the terahertz wave, high-speed feedback control is required. If such printers perform feedback control for each sheet of medium on such a printer, the load on the CPU becomes bigger, worsening the efficiency. In some cases, the speed of the feedback control limits the printing speed.

Image forming apparatus according to the first invention comprising: a stock unit for stocking a media stack made of a plurality of media with images formed on; an electromagnetic wave generation unit for generating a terahertz wave to radiate on the media stack; an electromagnetic wave detection unit for detecting the terahertz wave propagated in a laminating direction of the media stack; a memory unit for storing reference data; a processing unit for generating data related to an image forming state from the detection signal from the electromagnetic wave detection unit, information on the number of sheets of the medium, and information on the image formed on the medium; and a comparative unit for comparing the data generated by the processing unit and the reference data stored in the memory unit.

In view of the abovementioned problems, an printing method of the second invention for repeatedly printing the same information or the same unit of information on a plurality of sheets of media is characterized by having a printing step, a radiating step, a detecting step, a processing step, a storing step, a comparative/judgment step and a print controlling step.

In the printing step, the information is printed on the plurality of media.

In the radiating step, a terahertz wave is radiated on the media stack of the plurality of printed media so that the terahertz wave passes through at least the plurality of sheets of media.

In the detecting step, the terahertz wave propagated in the laminating direction of the media stack is detected.

In the processing step, the detection signal obtained in the detecting step is converted into data indicating the print states of the information on the plurality of media.

In the storing step, reference data for judging the print states of the information on the plurality of media is stored.

In the comparative/judgment step, the data obtained in the processing step and the reference data in the storing step are compared and the print states of the information on the plurality of media are judged.

In the print controlling step, the printing conditions in the printing step are adjusted based on the result obtained in the comparative/judgment step. The print controlling step can be omitted, as it is performed as required in the second invention. For example, the result from the comparative/judgment step is output outside so that an operator can control the printing conditions based on the output result.

In view of the abovementioned problems, a print detecting method of the third invention for judging the print states in the printing for repeatedly printing the same information or the same unit of information on a plurality of media is characterized by having a radiating step, a detecting step, a processing step, a storing step and a comparative/judgment step. In the radiating step, a terahertz wave is radiated on the media stack of the plurality of printed media that are obtained in printing the information on the plurality of media so that the terahertz wave passes through at least the plurality of sheets of media. In the detecting step, the terahertz wave from the media stack is detected. In the processing step, the detection signal obtained in the detecting step is converted into data indicating the print states of the information on the plurality of media. In the storing step, reference data for judging the print states of the information on the plurality of media is stored. In the comparative/judgment step, the data obtained in the processing step and the reference data in the storing step are compared and the print states of the information on the plurality of media are judged.

In view of the abovementioned problems, printing apparatus of the fourth invention for repeatedly printing the same information or the same unit of information on a plurality of media is characterized by having a printing unit, a stock unit, an electromagnetic wave generation unit, an electromagnetic wave detection unit, a memory unit, a comparative unit and a print controlling unit. The printing unit prints the information on the plurality of media. The stock unit stocks a media stack of a plurality of printed media. The electromagnetic wave generation unit radiates a terahertz wave on the media stack of the plurality of printed media that are in the stock unit so that the terahertz wave passes through at least the plurality of sheets of media. The electromagnetic wave detection unit detects the terahertz wave from the media stack in the stock unit. The processing unit converts the detection signal obtained in the electromagnetic wave detection unit into data indicating the print states of the information on the plurality of media. The memory unit stores reference data for judging the print states of the information on the plurality of media. The comparative unit compares the data generated by the processing unit and the reference data in the memory unit and judging the print states of the information on the plurality of media. The print controlling unit adjusts printing conditions in the printing unit based on a result obtained in the comparative unit.

In view of the abovementioned problems, print detecting apparatus of the fifth invention for repeatedly printing the same information or the same unit of information on a plurality of media is characterized by having an electromagnetic wave generation unit, an electromagnetic wave detection unit, a processing unit, a memory unit and a comparative unit. The electromagnetic wave generation unit radiates a terahertz wave on the media stack of the plurality of printed media that are obtained in printing the information on the plurality of media so that the terahertz wave passes through at least the plurality of sheets of media. The electromagnetic wave detection unit detects the terahertz wave from the media stack. The processing unit converts the detection signal obtained in the electromagnetic wave detection unit into data indicating the print states of the information on the plurality of media. The memory unit stores reference data for judging the print states of the information on the plurality of media. The comparative unit compares the data obtained in the processing unit and the reference data in the memory unit and judging the print states of the information on the plurality of media.

According to the present invention, a terahertz wave is propagated on printing media that make the predetermined number of media stacks (layers of media such as sheets of paper with toner or ink thereon after printing) in the laminating direction. The characteristics of the media stack of the printing media are monitored according to changes in the propagation state of the terahertz wave. As the present invention radiates the terahertz wave on the printing media forming a media stack as a way of monitoring the print state in this manner, the region that effects each other with the terahertz wave narrow. That makes it easier to detect the characteristics of the media stack made of printing media.

Further features of the present invention will become apparent from the following description of exemplary embodiments with reference to the attached drawings.

DESCRIPTION OF THE EMBODIMENTS

Embodiments of the present invention will be described with reference to the drawings.

First Embodiment

Image Forming Apparatus

Figure 6:
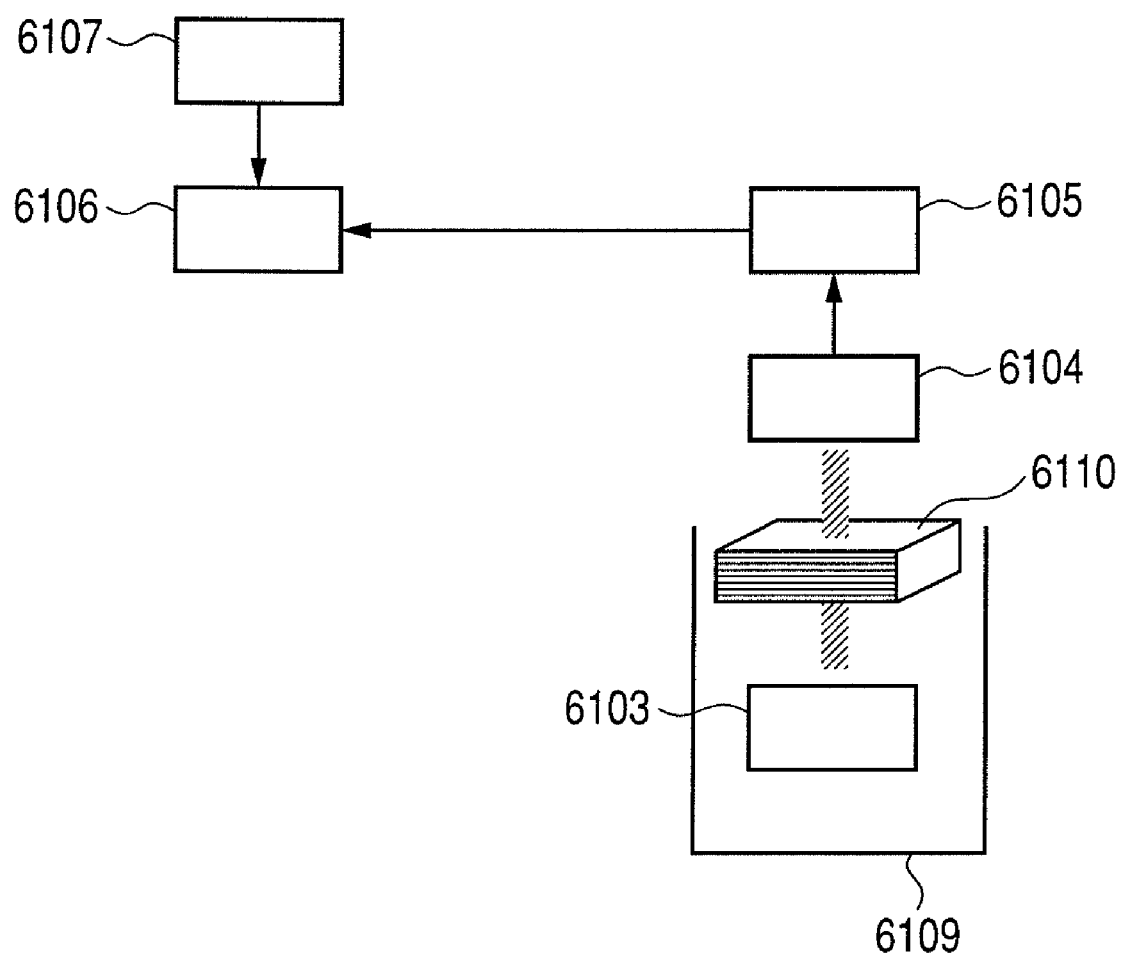
FIG. 6 is a block diagram for illustrating image forming apparatus, printing apparatus and a method for the same according to the present invention.

Image forming apparatus according to the embodiment will be described with reference to FIG. 6. The figure shows a stock unit 6109 for stocking a media stack 6110 made of a plurality of media with images formed on; and an electromagnetic wave generation unit 6103 for generating a terahertz wave to radiate on the media stack 6110. The figure further shows an electromagnetic wave detection unit 6104 for detecting the terahertz wave propagated in a laminating direction of the media stack 6110; and a memory unit 6107 for storing reference data. The figure also shows a processing unit 6105 for generating data related to an image forming state from the detection signal from the electromagnetic wave detection unit 6104, information on the number of sheets of the medium, and information on the image formed on the medium.

The data generated by the processing unit 6105 and the reference data stored in the memory unit 6107 are compared in a comparative unit 6106 in the figure. Then, the information on the compared result at the comparative unit 6106 is input in a controlling unit for controlling the printing conditions so that the information can be output outside to an operator. It is a matter of course that the compared result at the comparative unit can be stored in order. If the compared result is stored in order, the throughput of the image forming apparatus used (for example, how an image changes according to the number of sheets printed) can be recognized.

As the terahertz wave output from the electromagnetic wave generation unit 6103 is radiated in the laminating direction of the media stack 6110 in the embodiment, effects between the terahertz wave and a material present in the propagating direction of the terahertz wave (such as a media including paper, ink or toner forming an image) sufficiently appear.

In the processing unit 6105, data relating to the image forming state is generated in consideration of the information on the number of all the sheets of paper that form the media stack 6110 and the information on the image formed on the media.

The information on the number of media includes the information on the number of all the sheets of paper that form the media stack 6110 or the information on the number of books if the media stack is made of a plurality of books. With the information on the number of the media, whether the terahertz wave signal passed through ten sheets of paper or 500 sheets of paper can be recognized in advance. That improves the accuracy in the case where data relating to the image forming state is generated.

It is a matter of course that data relating to the image forming state is generated in consideration of the information on the number of media that form the media stack 6110 if the information on the number of sheets is not input in the processing unit each time when the data relating to the image forming state is generated as the number of media forming the media stack is predetermined.

The information on the image formed on the medium may be the information indicating that the same image is formed on a plurality of media or may include the information on the kind of image (for example, information on where ink or toner is present in an in-plane direction of the medium). The same image needs not be formed on a plurality of media forming a media stack. Different images may be formed on a plurality of media respectively if only the information on which image is formed on where is previously known. From the viewpoint of reducing the number of pieces of data, a terahertz wave is preferably radiated for obtaining the detection signal in the state where the same image is formed on all the media forming a media stack. The number of media for forming a media stack may be set to 10, 50, 500 or 1000 as required according to the intensity of the terahertz wave to radiate.

It is a matter of course that data relating to the image forming state is generated in consideration of the information on the image formed on the media if the image information is not input in the processing unit each time when the data relating to the image forming state is generated as the image formed on the media forming the media stack is predetermined.

The reference data stored in the memory unit and the data generated in the processing unit can be obtained in the manner below.

When the same image is formed on all the media, reference data forms the media stack made of the first to the 100$^{th}$ media on which the image is formed. Then, the terahertz wave is radiated on the media stack, the terahertz wave signal output via the media stack is received, and intensity data on a particular waveband is made the reference data. For the data generated in the processing unit, the media stack is made of the 501$^{st}$ to the 600th media, the terahertz wave is radiated on the media stack, the terahertz wave signal output via the media stack is received, and intensity data on a particular waveband is made the generated data. The reference data and the generated data are compared, and if they differ by 10%, for example, processing for adjusting the image forming conditions may be performed.

The technical matter described in a second embodiment or embodiments to be described later can be applied to the electromagnetic wave generation unit 6103, the stock unit 6109, the electromagnetic wave detection unit 6104, the processing unit 6105, the comparative unit 6106 and the memory unit 6107, unless the technical matter technically contradicts the units. An image forming unit adopting an electrophotographic system to be described later or a system for discharging ink is provided for the image forming apparatus described in the embodiment as required.

Second Embodiment

Printing Apparatus, Printing Method

Figure 1:
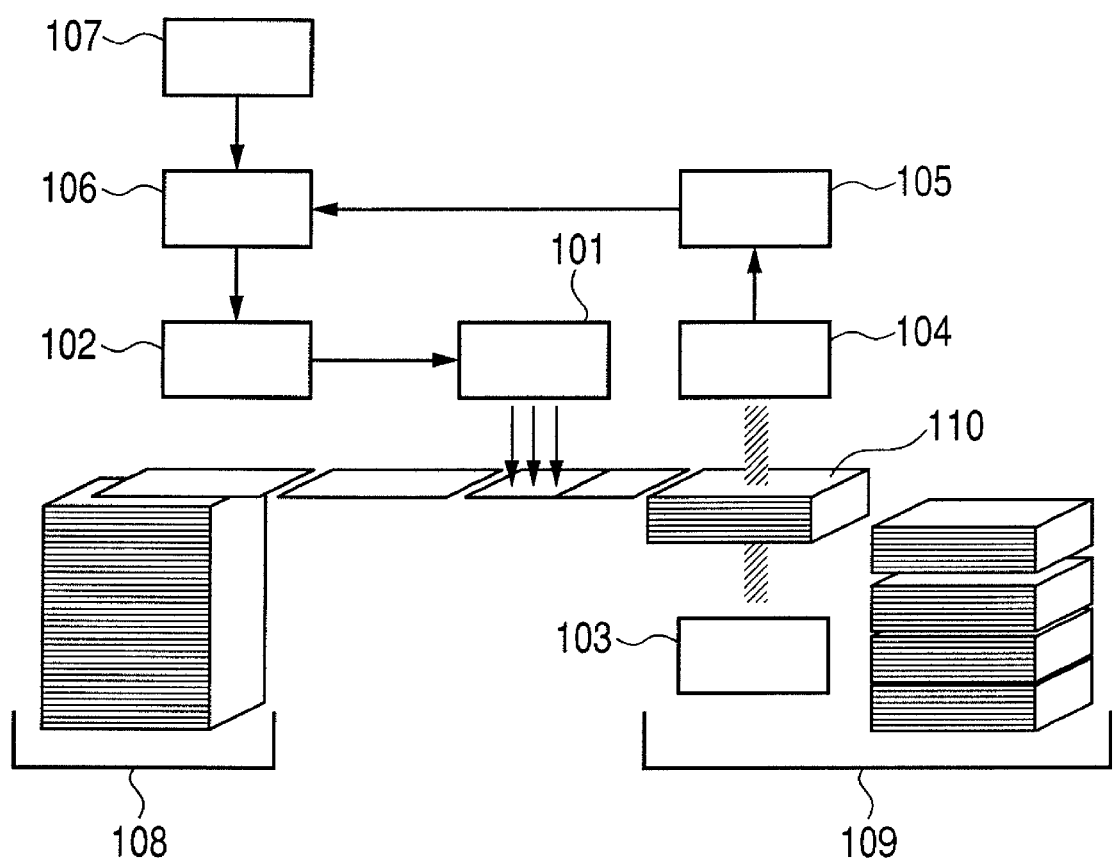
FIG. 1 is a block diagram for illustrating an image forming apparatus, a printing apparatus and a method for the same according to the present invention.

FIG. 1 is a block diagram of an embodiment of image forming apparatus and a printing method of the present invention. As shown in FIG. 1, the printing apparatus of the embodiment includes a printing unit 101, a print controlling unit 102, an electromagnetic wave generation unit 103, an electromagnetic wave detection unit 104, a processing unit 105, a comparative unit 106, a memory unit 107, a paper feeding unit 108 and a paper discharge unit 109. The printing unit 101 is for forming an image on a certain printing medium with ink or toner as in the inkjet system or an electrophotographic system. Here, the same information is repeatedly formed on a predetermined number of a plurality of media. In the case of a unit of printed matters made as a predetermined number of different printed matters are combined as a book (the information forming the unit of printed matters is referred as unit information), the unit information is repeatedly formed. Accordingly, any system may be adopted for the printing unit 101 instead of those described above if only the system can achieve the object of forming an image on a certain medium.

The print controlling unit 102 is for adjusting and controlling the image forming conditions in the printing unit 101. In the case of the inkjet system, the print controlling unit 102 controls an ink ejecting algorithm or a paper feeding speed. In the case of the electrophotographic system, it performs control on the amount of toner supply or charge control. Those described in the specification are only an example and the unit is not limited to them if only it can achieve the object of adjusting and changing the print state in the printing unit 101.

The electromagnetic wave generation unit 103 has a function of generating a high frequency electromagnetic wave and radiating the wave on a printed matter. In the present invention, the terahertz wave is specifically used as the high frequency electromagnetic wave. The terahertz wave has characteristics of permeability on a substance of the high frequency electromagnetic wave and a property of light traveling straight forward. Therefore, the terahertz wave has a good permeability on a non-conductive material such as paper. It is known that absorption lines for various materials are present in the electromagnetic waveband in the region with quite high sensitivity to moisture detection. By making use of the characteristics, the present invention can determine the kind of paper or detect moisture content or resistance of the paper with the terahertz wave, for example. The present invention can also detect the dryness, proportion of components, the total amount, a coating thickness and the like for chemical materials such as ink or toner. With characteristics of light, the present invention can freely manipulate the terahertz wave with such an optical element as a lens. With the characteristics, the present invention can obtain moist content distributing image in paper, for example.

In the embodiment, the electromagnetic wave generation unit 103 is placed near the paper discharge unit 109 as shown in FIG. 1. The paper discharge unit 109 corresponds to an output tray or a finisher.

In this specification, paper will represent a printing medium hereinafter. The printing medium is not limited to paper, however. Any material may be used as the printing medium if only it makes a printing medium, through which the terahertz wave passes, like a printed matter used for clothes. In the embodiment, the terahertz wave generated from the electromagnetic wave generation unit 103 is propagated in the laminating direction of a bundle of paper 110 stacked in the paper discharge unit 109 so that the terahertz wave passes at least multiple sheets as shown in FIG. 1.

As a method for generating the terahertz wave, an antenna structure formed on a semiconductor substrate, for example, is used. In the embodiment, GaAs substrate of the thickness of 100 μm with LT-GaAs epitaxial growth layer of the thickness of 1.5 μm is used as a semiconductor substrate. A dipole antenna structure with a clearance of 5 μm in the center is used as an antenna structure. The dipole antenna structure is created in a general evaporating process using AuGe/Ni/Au for materials into an antenna length of 30 μm.

It is a matter of course that the antenna structure is not limited to that described here, either. The size and shape of an antenna depends on the terahertz wave to be treated. In the embodiment, a bias is applied to the clearance of the antenna. The clearance is optically gated with a femtosecond laser. The electromagnetic wave generated at that moment is used as the terahertz wave. A terahertz wave generating method is not limited to the method, and any method such as a method for gating the clearance by using a different frequency of two kinds of lasers with different wavelengths or a method using a negative resistance element such as a quantum cascade laser can be used. An oscillator using a non-linear optical crystal or an oscillator using an electronic tube such as BWO (Backward-Wave Oscillator) can also be used.

The electromagnetic wave detection unit 104 is for detecting the terahertz wave passed and propagated through the bundle of paper 110, which is a media stack of printing media. The electromagnetic wave detection unit 104 is placed near the paper discharge unit 109 like the electromagnetic wave generation unit 103. In FIG. 1, the electromagnetic wave detection unit 104 is placed as almost facing the electromagnetic wave generation unit 103 across the bundle of paper 110. The electromagnetic wave detection unit 104 is not necessarily placed like this, however. An optical system increases the freedom in arranging the unit if optical characteristics of the terahertz wave are used. In some cases, the electromagnetic wave detection unit 104 needs not to be placed near the paper discharge unit 109 either. An optimal arrangement may be selected in consideration of the intensity of the terahertz wave signal or attenuation due to the measuring environment.

The detection unit 104 for the terahertz wave has the same configuration as that of the electromagnetic wave generation unit 103. A bias is applied to the clearance of the antenna. The clearance is optically gated with a femtosecond laser for detecting the terahertz wave. The unit is not limited to use that method as the electromagnetic wave generating unit 103 is not. The unit may use a method using a heat detector such as a bolometer or electric-optic effects. The unit may also use a method using a negative resistance element like a Schottky diode.

Although the electromagnetic wave generation unit 103 and the electromagnetic wave detection unit 104 are shown as a single unit respectively in FIG. 1, the units may be plural. Each of the electromagnetic wave generation unit 103 and the electromagnetic wave detection unit 104 may separately have a mechanism for mechanically scanning the bundle of paper 110 or a mechanism or a unit for controlling the directivity of an electromagnetic wave.

Figure 4:
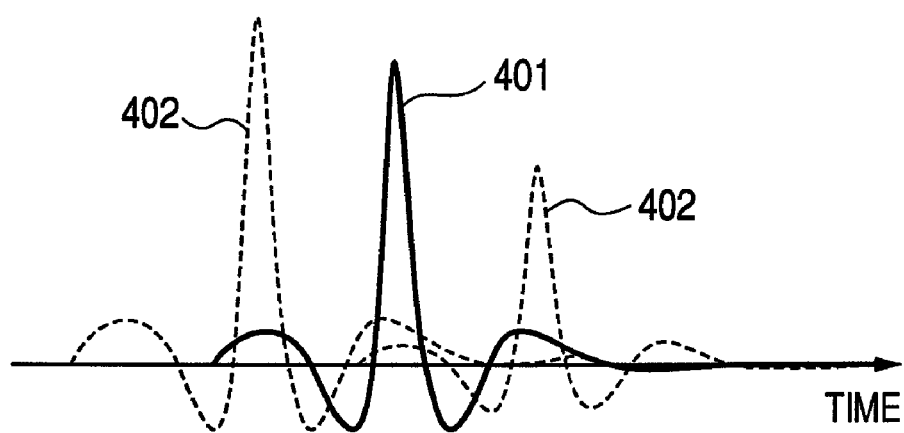
FIG. 4 is an image diagram of terahertz waves in a time region that changes according to the print state.

The processing unit 105 is for obtaining desired physical property data relating to the bundle of paper 110 by using the detection signal of the terahertz wave detected in the electromagnetic wave detection unit 104. The processing unit 105 obtains physical information by using the information on the intensity change, the phase shift or the waveform change of the detection signal 402 for a reference signal (referred signal 401) as shown in FIG. 4. The physical information that can be obtained includes the information on the moisture content of the paper, the resistance of the bundle of paper 110 based on the moisture contents, the dryness of toner or ink, and the coating thickness. Such information can be obtained in the propagating direction of the terahertz wave in the bundle of paper 110.

Figure 5:
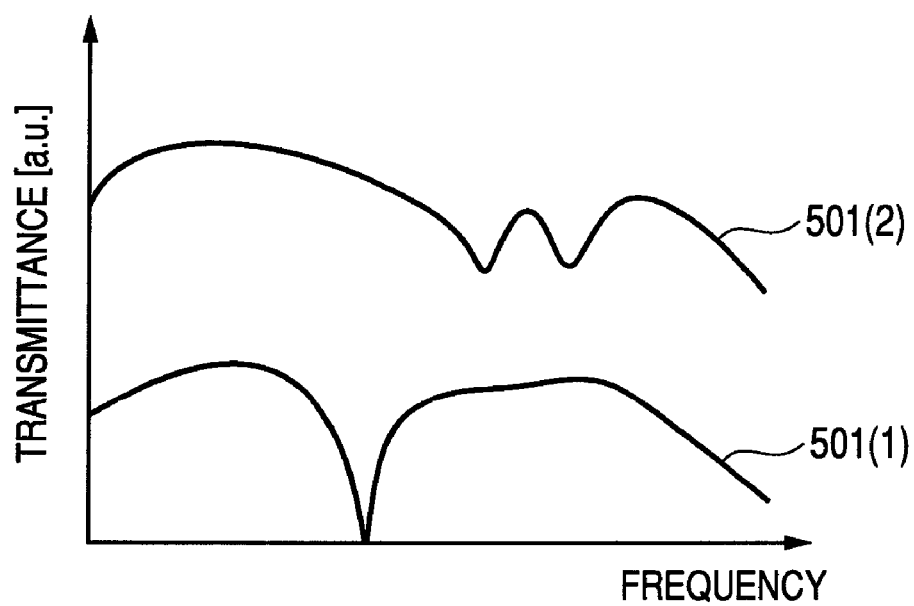
FIG. 5 is an image diagram of terahertz waves in a frequency region that changes according to the print state.

As shown in FIG. 5, the signal in the time region is converted into the signal in the frequency region so that the physical information can be obtained from a change in the signal against the referential signal (for example, a difference in the spectrum (2) 502 against the spectrum (1) 501). As the physical information that can be obtained, the information on the kind of paper, the color or the total amount of toner or ink or the information in the propagating direction of the terahertz wave in the bundle of paper 110 can be obtained other than the information described above. As a method for obtaining the information, a method of obtaining the proportion of toner or ink from the obtained spectrum, comparing the proportion with a color lookup table prepared in the processing unit 105 and judging the information can be taken. As parameters regarding printing only need to be detected by the terahertz wave in the invention, it is a matter of course that the physical information is not limited to those described above. A method for deciding a color is not limited to those mentioned above, either.

Although a pulse signal of the terahertz wave is converted so that the spectrum information is obtained here, a method for that purpose is not limited to that method. If the wavelengths for changing the abovementioned parameters relating to the print state in characteristic manner are known, the method below may be taken. The intensity of each wavelength is monitored by using terahertz serial waves of a plurality of wavelength corresponding to the known wavelengths so that a change in characteristics of the parameters can be estimated based on the change in intensity of each wavelength.

If the source of the terahertz serial waves has wavelength variability, a method for obtaining characteristics by shifting the spectrum near a part or all of the arbitrary wavelengths shown in FIG. 5 may be taken. If such terahertz serial waves with wavelength variability are used, the abovementioned characteristic wavelengths need not to be obtained at a time. For example, a method for adjusting the wavelengths of the terahertz serial waves for each characteristic wavelength region and detecting the changes for a plurality of times to detect a plurality of intensity changes may also be used. The parameter to be obtained may be plural instead of one.

As mentioned above, in the embodiment, one or both of the electromagnetic wave generation unit 103 and the electronic wave detection unit 104 may have a unit of scanning the terahertz wave. In such a case, the processing unit 105 may plot the physical information at each scanning point and perform imaging processing on the result. The image obtained here corresponds to the physical information in the laminating direction on the bundle of paper 110 converted into two-dimensional information.

As mentioned above, the processing unit 105 first obtains the signals in chronological order or in the frequency region from the signals in the electronic wave detection unit 104. Then, the unit 105 extracts the characteristic physical information relating to the bundle of paper 110 from the obtained signals. Although the pulsing signals are mainly described specifically as the terahertz wave, the signals are not limited to them. The terahertz waves used may be a serial wave. The serial wave may be plural. If a plurality of terahertz waves are used, a method for monitoring the frequency points characterized by the physical information on the bundle of paper 110 for estimating the print state of the bundle of paper 110 may be used. A method for improving the sensitivity by obtaining difference signals of a plurality of pieces of physical information may also be used.

The comparative unit 106 is for comparing the physical information on the bundle of paper 110 obtained in the processing unit 105 and the referential physical information and sending the information on a change in the state of the bundle of the paper 110 to the print controlling unit 102. The referential physical information is saved in the memory unit 107 as reference data. In the embodiment, information on the printed matter or information on the terahertz wave used is considered as reference data. The information on the printed matter includes the kind of paper, image data, a target value for toner or ink to be applied and environment (moisture content), for example. The information on the terahertz wave includes a change or a phase change of the amount transmitted against the initial value. In the embodiment, the target value for toner or ink to be applied (how much the image quality to be obtained is near the desired image quality) will be mainly described as an object to be controlled among the objects to be controlled. The print control unit 102 adjusts and controls the printing unit 101 so as to bring the value to the target value. The kind of the reference data or the object to be controlled is not limited to those described here.

The referential physical information can be obtained in the obtaining method shown below. Predetermined physical information that can be obtained from a response of the terahertz wave from the bundle of a predetermined number of sheets of paper 110 present in the paper discharge unit 109 is considered as reference information and stored in the memory unit 107. In some cases, an initial print state may be determined according to a response of the terahertz wave and a database of the kinds of paper and the type of printing (character, photograph, graphics) matched each other. That is, any method can be used if only the method can determine the initial print state from the response of the first terahertz wave. The comparative unit 106 sends the difference information between the physical information on the bundle of paper obtained in the processing unit and the reference physical information to the print controlling unit 102 for each unit of a predetermined number of sheets (the same information or the same unit of information is printed on the predetermined number of sheets) and controls the print state so as to minimize the difference.

The method for obtaining the referential physical information is not limited to that described above. For a printer with a scanner, the referential physical information relating to the bundle of a predetermined number of sheets of paper 110 may be predicted or estimated by using the electronic information on the printing unit captured by the scanner. If the electronic information is created by a personal computer or captured in a portable device such as a digital camera, the referential physical information relating to the bundle of a predetermined number of sheets of paper 110 may be predicted by using the electronic information in advance. In some cases, the print state may be determined according to the previously predicted information and the database of the kind of paper or the type of printing (character, photograph, graphics) matched each other. That is, any method can be used if only the method can determine the print state from the electronic information on the printed matter. The comparative unit 106 also sends the difference information between the physical information on the bundle of paper obtained in the processing unit and the referential physical information to the print controlling unit 102 for each unit of a predetermined number of sheets and adjusts and controls the print state so as to minimize the difference.

Although the information set in the initial stage of printing or before printing is fixedly used for the referential information here, the referential information is not limited to those described above. An average of physical values obtained in a predetermined number of times of the printing operation (a predetermined number of sheets are printed for each cycle of printing in the printing operation) may be used as the referential information. Strictly speaking, as the referential information is obtained from the print state of a predetermined number of times of printing including the latest print state, the referential information is serially updated. Here, the comparative unit 106 and the print controlling unit 102 control the print state so that the referential information becomes stable in the long run (for example, so as to remove a drift component).

The paper feeding unit 108 has a function of stocking sheets of paper used for printing and sending the sheet of paper to the printing unit 101 that actually performs the printing operation. The printer satisfies the fundamental requirements as a printing apparatus by the print controlling unit 102 for adjusting and controlling of the printing operation of the printing unit 101 and the paper discharge unit 109 for stocking the printed matters in addition to the printing unit 101 and the paper feeding unit 108. The embodiment further has a mechanism for causing the terahertz wave to be propagated in the laminating direction of the media stack of the products that is, a bundle of paper 110 stored in the paper discharge unit 109. The embodiment is for obtaining a change of the physical information of the media stack from the referential information according to the change in the propagating state of the terahertz wave and causing the print controlling unit 102 to change the print state so that the change is kept the same, or kept in a certain range.

Now, basic operations regarding the printing apparatus of the embodiment will be collectively described. First, the paper feeding unit 108 feeds sheets of paper to the unit that performs printing, i.e., the printing unit 101. The printing unit 101 prints a desired printing pattern on the sheets of paper. That is, the printing unit 101 repeatedly prints the same information or the same unit of information on a predetermined number of sheets of paper. Here, the print controlling unit 102 controls the printing unit 101 according to predetermined printing conditions. The set conditions are manually or automatically set or measured according to the image data in advance. In the embodiment, the printing conditions are set according to the kind of paper to be used and the kind of ink or toner. A change of the print state of the obtained printed matter in the printing step is corrected.

If the abovementioned printing conditions are not suitable for actual printing, the printing conditions can be corrected. If the set kind of paper is different, the kind of paper is determined according to the kind and the amount of calcium carbonate, which is a major component of paper, and the print state can be changed as required. If the kind of toner or ink is different, the kind of toner or ink is determined according to the propagation information of the terahertz wave, and the print state can be changed to suit the kind as required. In such a case, it is desirable to set the referential information again according to the updated printing conditions.

The sheet of paper printed in the printing unit 101 is ejected to the paper discharge unit 109. The printing operations are performed in order until the sheets by the number set by a user are printed. The paper discharge unit 109 preferably has a function of temporarily stocking printed matters as a finisher.

If the user sets the number of sheets in advance, the electromagnetic wave generation unit 103 placed near the paper discharge unit 109 radiates the terahertz wave on the bundle of a predetermined number of sheets of printing paper 110 in the paper discharge unit 109 so that the terahertz wave passes at least a plurality of sheets. Then the terahertz wave propagated through the bundle of paper 110 is detected by the electromagnetic wave detection unit 104 near the paper discharge unit 109. As mentioned above, the electromagnetic wave generation unit 103 and the electromagnetic wave detection unit 104 need not necessarily be placed near the paper discharge unit 109.

The terahertz wave detected at the electromagnetic wave detection unit 104 is converted into a predetermined signal form by the processing unit 105. From the signals, the physical values indicating the print states of the bundle of paper 110 are obtained. For example, the signals are converted into data of the terahertz wave in chronological order and the physical values are obtained from data of the intensity change, the phase change or both of them as shown in FIG. 4. Alternatively, the signals are converted into frequency spectrum data and the physical values are obtained from data of the intensity change, the phase change or both of them in each frequency as shown in FIG. 5.

If the physical value is first obtained according to the change in a propagating state of the terahertz wave, the information on the initial print state is saved in the memory unit 107 as reference data by using the data. Then, a difference between the physical property data obtained thereafter and the reference data is obtained at the comparative unit 106 and the correction information is sent to the print controlling unit 102. That is, examination information on the bundle of paper 110 by the terahertz wave for the first time is not used in controlling the printing unit 101. The print state of the printing unit 101 is controlled with the information on the examined results of the second and later times and the first examined result. As mentioned above, a method for obtaining the reference data stored in the memory unit 107 is not limited to that. If the reference data is previously obtained, the print state can be controlled according to the first examined results. If the reference data is obtained from the examined results for a predetermined number of times, the print state of the printing unit 101 is not controlled at the examining step in the printing step, in which the number of printing on a predetermined number of sheets of paper has not reached the predetermined number of times.

When the examination by the terahertz wave has been done, the paper discharge unit 109 moves the bundle of paper 109 to a desired place and stocks the predetermined number of printed matters. In some cases, the bundle of paper 109 that has been used in examination needs not to be moved. A bundle of paper 109 that has not been examined may be laminated on the bundle of paper 109 used in examination. In such a case, the processing unit 105 or the comparative unit 106 corrects the physical property information indicating the print state according to the number of bundles of the bundles of paper 101.

The print controlling unit 102 adjusts and controls the printing unit 101 based on the correction information obtained from the comparative unit 106 so that the print state approaches a desired state. At this moment, the print state needs not necessarily be made a desired state by an occasion of controlling. A method for gradually bringing the print state to the desired state by a plurality of occasions of controlling may be taken.

The printed matters used here need not necessarily be the same printed matter for each sheet. As a physical property value in the laminating direction of the bundle of paper 110 is monitored in the embodiment, all the printed matters used here only need to have the same contents as a whole.

As mentioned above, the embodiment monitors the print state by using the terahertz wave on the bundle of printed paper 110 and controls the printing unit 101 so as to bring the print state near to the desired print state. Therefore, the embodiment needs not to control the print state for each of the printed results on each medium as the conventional technique does. That easily speeds up the operation. The embodiment propagates the terahertz wave through the bundle of paper 110 by taking advantage of the permeability of the terahertz wave on paper. That increases the length to interact between the terahertz wave and paper ink or toner. Therefore the embodiment has effect in improving detection sensitivity.

As the terahertz has a strong absorbing power for moisture, it can detect moisture content of paper, toner or ink with high sensitivity. Based on the moisture content, dryness of toner or ink can be judged. As the wavelength of the terahertz wave corresponds to the wavelength of molecular vibration or lattice vibration, a difference in a structure of toner or ink can be examined according to the wavelength. The embodiment can judge the total amount of toner or ink of the bundle of printed matters by taking advantage of such properties, as described above. The embodiment can also separate the difference in structures of toner or ink to be used from the absorption spectrum and judge the color of the printed matters.

If the same operation is performed with light near the visible light, significant amount of light is required to pass through the bundle of printed matters. The embodiment, however, uses the terahertz wave that originally has good permeability. Therefore, the embodiment can reduce power requirement of the printing apparatus.

The high-speed printer for processing a great amount of printed matters requires an operator to control the print state of the printer according to the state of the printed matters or the surrounding environment. As the embodiment, however, can automate the operations conventionally performed by an operator, it also has effect in reducing the load on the operator.

Embodiments

Specific embodiments will be described below with reference to the drawings. The same components in the drawings are denoted by the same reference numerals.

Example 1

The example 1 shows an example of the printing apparatus according to the present invention applied to a copy machine adopting an electrophotographic system.

Figure 2:
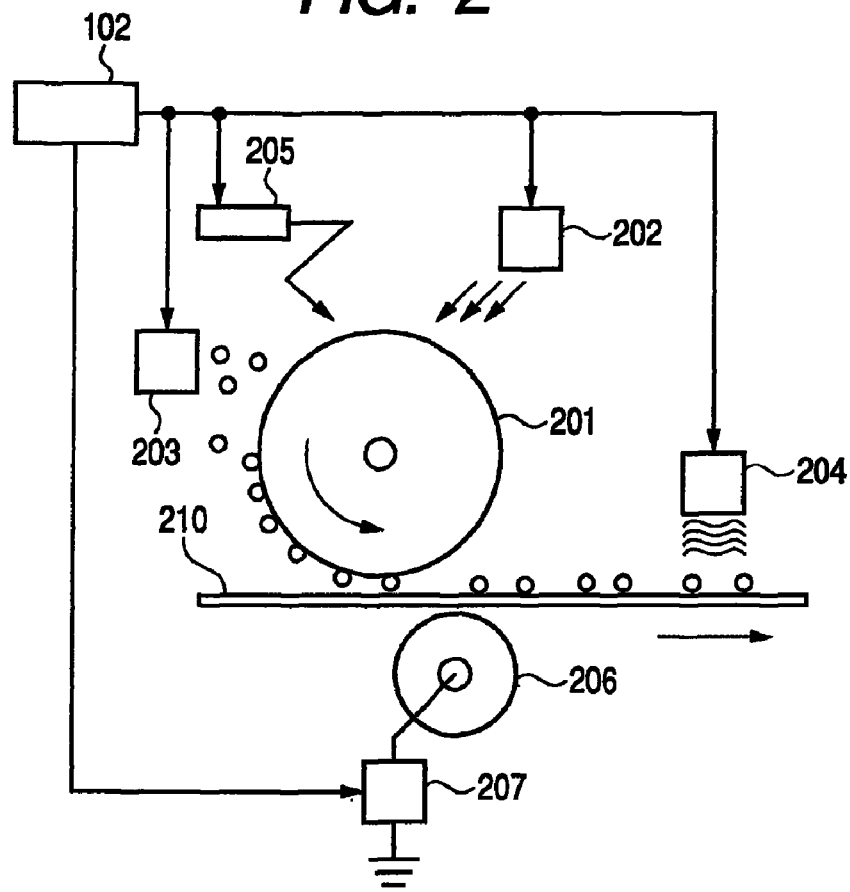
FIG. 2 is a schematic diagram for illustrating printing apparatus and a method for the same in a first embodiment.

FIG. 2 is a schematic diagram of printing apparatus and a method for the same in this example. The FIG. 2 shows the printing unit 101 shown in FIG. 1 more specifically. As the other components are basically the same as those shown in FIG. 1, they are omitted in FIG. 2. That is, the printing unit 1 shown in FIG. 1 is adapted as shown in FIG. 2. Accordingly, the step of detecting the print state of the bundle of paper 110 by using the terahertz wave propagated through the bundle of paper 110 is the same as that described in the embodiment.

In the example, the printing unit 101 includes a drum 201, a charge unit 202, a toner feeding unit 203, a fixing unit 204, an image forming unit 205, a transfer unit 206 and a transfer controlling unit 207 as shown in FIG. 2. Specifically, the operations that much contribute to printing on a sheet of paper can be adjusted and controlled by the print controlling unit 102 as shown in FIG. 2.

The drum 201 is a unit for applying toner in a desired pattern on a sheet of paper to transfer the pattern on the paper. The charge unit 202 is a unit for charging the drum 201 with desired electrical charge for applying toner. The amount of toner to be applied to the drum can be controlled as the charge unit 202 is controlled. The toner feeding unit 203 is a unit for feeding toner to a latent image of electrical charge present on the drum 201. The shades or color of print can be controlled as the amount of toner to be applied to the drum 201 is controlled. Although each unit of the drum 201 and the toner feeding unit 203 is described in the embodiment, the numbers of units are not limited to one. These units may be plural according to the kind of toner to be used.

The fixing unit 204 is a unit for fixing toner transferred on a sheet of paper by heat. The fixing state can be controlled as the fixing temperature is adjusted, for example. The image forming unit 205 is a unit for forming a latent image by radiating a laser on the electrical charge charged on the drum 201. The charged state on the drum 201 can be controlled as the laser intensity is adjusted. The transfer unit 206 is a unit for applying an electric field between the drum 201 and the transfer unit 206 for transferring the toner on the drum 201 to a sheet of paper 210. The electrical field is applied by the transfer controlling unit 207. The transferring state can be controlled as the electrical field is adjusted, for example.

The operations will be described below. As a method for printing on a sheet of paper using an electrophotographic system is generally known, it will be omitted from the description here. Which unit is to be controlled based on the abovementioned examined result of the print state by the terahertz wave will be described here.

Now, it is assumed that moisture content of the bundle of paper 110 is monitored in a manner using the terahertz wave. A change in the moisture content is strongly tied to the resistibility of paper. The resistibility of paper greatly contributes to transferring conditions or fixing conditions of toner on a sheet of paper. In this example, the print controlling unit 102 controls the units below so that the print state is kept constant without regard of any change in the moisture content in the bundle of paper 110. The print controlling unit 102 controls a voltage bias applied from the transfer controlling unit 207 to the transfer unit 206, for example. The print controlling unit 102 may control the charged amount of the drum 201 charged by the charge unit 202. The print controlling unit 102 may also control the fixing temperature of the fixing unit 204.

Now, it is assumed that the amount and the color of toner to be applied to the bundle of paper 110 are monitored in a manner using the terahertz wave. In this example, the print controlling unit 102 controls the units below so that the amount and the color of toner on the bundle of paper 110 are kept the same. The print controlling unit 102 controls electrical charge for a latent image to be charged to the drum 201 by controlling the voltage applied by the charge unit 202 and the laser intensity of the image forming unit 205, for example.

The print controlling unit 102 may also control the amount of toner fed from the toner feeding unit 203.

In this example, the print state is monitored according to the moisture content and the amount and color of toner in the bundle of paper 110 in the direction for an electromagnetic wave to propagate by using the terahertz wave that propagates through the bundle of paper 110 as mentioned above. Then, each unit for contributing the printing step is controlled so that the print state is kept constant.

A high-speed printer or the like has conventionally required a special operator to perform a series of controlling operations. As the example automates those operations, it has effect in reducing the load on the operator. If an operator performs adjusting operations in conventional devices, the operator cannot always stick to the adjusting operations. As the example performs the adjusting operations almost serially, it has effect in reducing the cases of imperfect printing. That improves reliability of printing. The abovementioned apparatus and the method may be used as the print detecting apparatus and the method for the same. If the apparatus and the method are applied to check a bound material, it can detect incorrect collating and missing pages as well as imperfect printing of the product. The apparatus and the method have effect in improving reliability of the products as they have a separate mechanism for removing such an imperfect product at the paper discharge unit 109.

Example 2

The example 2 shows an example of the printing apparatus according to the present invention applied to printer machine adopting an inkjet system.

Figure 3:
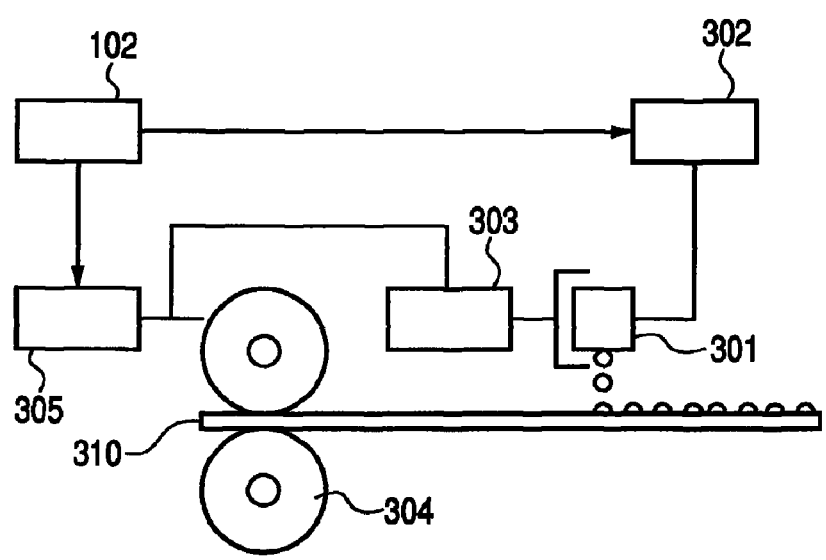
FIG. 3 is a schematic diagram for illustrating printing apparatus and a method for the same in a second embodiment.

FIG. 3 is a schematic diagram of printing apparatus and a method for the same in this example. FIG. 3 shows the printing unit 101 shown in FIG. 1 more specifically with the other components omitted. As the step of detecting the print state of the bundle of paper 110 by using the terahertz wave propagated through the bundle of paper 110 is the same as that described in the above described embodiment, it is omitted from the description here.

In the example, the printing unit 101 includes an ejection unit 301, an ejection controlling unit 302, a scan mechanism unit 303, a paper feeding unit 304 and a scan controlling unit 305 as shown in FIG. 3. Specifically, the operations that much contribute to printing on a sheet of paper 310 can be controlled by the print controlling unit 102 as shown in FIG. 3.

The ejection unit 301 is a head part of an inkjet for ejecting desired ink on the sheet of paper 310. The ejection controlling unit 302 is a unit for controlling an ejecting algorithm of the ejection unit 301. The color or amount of ink printed on the sheet of paper 310 is controlled as the ejecting algorithm is controlled. The scan mechanism unit 303 is a mechanism for mechanically moving the ejection unit 301 vertical to the paper feeding direction. The paper feeding unit 304 is a mechanism for mechanically sending out the sheet of paper 310. The operations of the mechanisms are controlled by the scan controlling unit 305.

The operations will be described below. As a method for printing on a sheet of paper using an inkjet system is generally known, it will be omitted from the description here. Which unit is to be controlled based on the abovementioned examined result of the print state by the terahertz wave will be described here.

In the inkjet system, the amount of ink ejected from the ejection unit 301 is basically decided. As a method for controlling the print state, the ejecting algorithm by the ejection controlling unit 302 (for example, an ejecting speed, an ejecting direction, an ejecting interval, the total amount of ejection, proportion of all kinds of ink) and the scanning method by the scan controlling unit 305 are collectively adjusted and controlled. It is assumed that dryness of ink is monitored according to the moisture content in a manner using the terahertz wave. In this example, the feeding speed of the paper feeding unit 304 is changed by the scan controlling unit 305 to secure a time for drying the ink. Here, the ejecting algorithm is changed at the ejection controlling unit 302 according to the feeding speed of the paper 310.

Now, it is assumed that the total amount and the color of ink applied to the bundle of paper 110 are monitored in a manner using the terahertz wave. In this case, the print state is brought near to a desired print state as the amount of ink and proportion of kinds of ink ejected from the ejecting unit 301 are controlled by the ejection controlling unit 302. Here, the scanning time period or a pattern for the ejecting unit 301 is changed by the scan controlling unit 305.

In this example, the print state is monitored according to the moisture content and the amount and color of ink in the bundle of paper 110 in the direction for an electromagnetic wave to propagate by using the terahertz wave that propagates through the bundle of paper 110 as mentioned above. Then, each unit for contributing the printing step is controlled so that the print state is kept constant.

A conventional inkjet printer provided a margin in a printing time for each sheet in order in order for the printed matter to be completely dried. That limited the printing speed. In the embodiment, dryness of the printed matter is monitored according to the print state and the print state is controlled. Therefore, the embodiment has effect in increasing the printing speed for some degree of dryness of the printed matter.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-246196, filed Sep. 12, 2006 which is hereby incorporated by reference herein in its entirety.

What is claimed is:

1. An image forming apparatus comprising:
    a stock unit for stocking a plurality of printed matter printed by the image forming apparatus;
    an electromagnetic wave generation unit for generating a terahertz wave to radiate into the printed matter;
    an electromagnetic wave detection unit for detecting the terahertz wave propagated in a laminating direction of the printed matter;
    a memory unit for storing reference data;
    a processing unit for generating data, which is related to an image forming state, from a detection signal of the electromagnetic wave detection unit, information on the number of sheets of the printed matter, and information on the image formed on the medium; and
    a comparative unit for comparing the data generated by the processing unit and the reference data stored in the memory unit.

2. A printing method for repeatedly printing the same information or the same unit of information on a plurality of media comprising:
    a printing step of printing the information on the plurality of media to form a plurality of printed matter;
    a radiating step of radiating a terahertz wave into the printed matter so that the terahertz wave passes through at least the plurality of printed matters;
    a detecting step of detecting the terahertz wave propagated in the laminating direction of the printed matter;
    a processing step of converting the detection signal obtained in the detecting step into data indicating the print states of the information on the plurality of sheets of printed matter;
    a storing step of storing reference data for judging the print states of the information on the plurality of printed matter; and
    a comparative/judgment step of comparing the data obtained in the processing step and the reference data in the storing step and judging the print states of the information on the plurality of printed matter.

3. The printing method according to claim 2, further comprising
    a print controlling step of adjusting printing conditions at the printing step based on a result obtained at the comparative/judgment step.

4. The printing method according to claim 3, wherein
    the reference data stored at the storing step is such that an initial print state of the printed matter is obtained from a first detection signal from the terahertz wave detected at the detecting step and stored as the reference data.

5. The printing method according to claim 3, wherein
    the reference data stored at the storing step is such that a response of the printed matter to the terahertz wave and the print state of the plurality of media are estimated from prepared electronic information on the information and stored as the reference data.

6. The printing method according to claim 3, wherein
    the reference data stored at the storing step is such that the print state of the printed matter is obtained from the detection signals from the terahertz waves detected for a plurality of number of times including the latest detection signals from the terahertz wave detected at the detecting step and stored as the reference data.

7. Printing apparatus for repeatedly printing the same information or the same unit of information on a plurality of media comprising:
    a printing unit for printing the information on the plurality of media to form a plurality of printed matter;
    a stock unit for stocking the plurality of printed matter printed by the printing unit;
    an electromagnetic wave generation unit for generating a terahertz wave to radiate into the printed matter which are in the stock unit so that the terahertz wave passes through at least the plurality of printed matter;
    an electromagnetic wave detection unit for detecting the terahertz wave propogated in a laminating direction from the printed matter in the stock unit;
    a processing unit for converting the detection signal of the electromagnetic wave detection unit into data indicating the print states of the information on the plurality of printed matter;
    a memory unit for storing reference data for judging the print states of the information on the plurality of printed matter;
    a comparative unit for comparing the data generated by the processing unit and the reference data in the memory unit and judging the print states of the information on the plurality of printed matter; and
    a print controlling unit for adjusting printing conditions in the printing unit based on the result obtained in the comparative unit.

* * * * *